(12) United States Patent
Aoki et al.

(10) Patent No.: US 7,985,407 B2
(45) Date of Patent: Jul. 26, 2011

(54) METHOD OF TREATING SOLID TUMOR

(75) Inventors: Kazunori Aoki, Tokyo (JP); Teruhiko Yoshida, Tokyo (JP)

(73) Assignee: National Cancer Center, Tokyo (JP)

( * ) Notice: Subject to any disclaimer, the term of this patent is extended or adjusted under 35 U.S.C. 154(b) by 977 days.

(21) Appl. No.: 11/857,667

(22) Filed: Sep. 19, 2007

(65) Prior Publication Data

US 2009/0074727 A1     Mar. 19, 2009

(51) Int. Cl.
*A01N 65/00* (2009.01)
*A61K 48/00* (2006.01)
*C12N 5/00* (2006.01)
*C12N 15/00* (2006.01)
*C12P 21/06* (2006.01)

(52) U.S. Cl. .................. 424/93.1; 424/93.2; 424/93.21; 435/320.1; 435/325; 435/455; 435/69.1

(58) Field of Classification Search ........................ None
See application file for complete search history.

(56) References Cited

U.S. PATENT DOCUMENTS

| 7,514,416 B2 | 4/2009 | Aoki et al. |
| 2005/0260167 A1 | 11/2005 | Aoki et al. |
| 2009/0175825 A1 | 7/2009 | Aoki et al. |

OTHER PUBLICATIONS

Narumi et al, Cancer Science 101:1686-1694, 2010.*
Hara et al, Immunol Immunother 58:1007-1021, 2009.*
H. Hara et al., Proceedings of the Sixty-Fifth Annual Meeting of the Japanese Cancer Association, Sep. 20, 2006, Poster Presentation (P), Session 21-5, P-1245.
K. Aoki et al., 13th Annual Meeting of the Japan Society of Gene Therapy, Jun. 12-14, 2007, Oral Presentation 6, Abstract 48.
Niwa et al., "Efficient selection for high-expression transfectants with a novel eukaryotic vector," Gene, vol. 108(2), pp. 193-199, 1991.
English language abstract of K. Aoki et al., 13th Annual Meeting of the Japan Society of Gene Therapy, Jun. 12-14, 2007, Oral Presentation 6, Abstract 48.
H. Hara et al., Proceedings of the Sixty-Fifth Annual Meeting of the Japanese Cancer Association, Sep. 30, 2006, Poster Presentation (P), Session 21-5, P-1245, along with an English language translation.

* cited by examiner

*Primary Examiner* — Sumesh Kaushal
(74) *Attorney, Agent, or Firm* — Greenblum & Bernstein, P.L.C.

(57) ABSTRACT

The present invention provides a method of immune/gene combination therapy that has an effect of suppressing growth of an intractable solid tumor and is useful for treatment of such a tumor, and a therapeutic composition used for said method.

6 Claims, 8 Drawing Sheets

METHOD OF TREATING SOLID TUMOR

BACKGROUND OF THE INVENTION

1. Field of the Invention

The present invention relates to a method of immune/gene combination therapy that has an effect of suppressing growth of an intractable solid tumor and is useful for treatment of such a tumor, and a therapeutic composition used for said method.

2. Description of Related Art

Allogeneic hematopoietic stem cell transplantation (alloHSCT) often leads to a significant graft-versus-tumor (GVT) effect, and has proven to be an effective therapeutic approach for several types of leukemia, particularly acute and chronic myelogenous leukemia. Recently, alloHSCT has been applied not only for hematological malignancies but also for solid cancers such as renal and breast cancers. However, the benefit of the GVT effect is often offset by the occurrence of graft-versus-host disease (GVHD), a potentially fatal adverse effect primarily mediated by donor T cells. It is commonly believed that in MHC-matched alloHSCTs the target antigens for a GVT effect include tumor-associated antigens (TAAs) and ubiquitously or tissue-specifically expressed minor histocompatibility antigens (mHAs), whereas the targets for GVHD are mHAs. Therefore, efforts to selectively enhance a donor T cell response to TAAs may provide a means to augment antitumor activity without a concomitant increase in toxicity.

The interferon alpha (IFN-α) protein is a cytokine with pleiotropic biological properties that include antiviral activity, regulation of cell proliferation, induction of apoptosis and immunomodulation. The cytokine has been used worldwide for treatment of a variety of cancers including certain hematological malignancies such as chronic myeloid leukemia and solid tumors such as melanoma and renal carcinoma. However, clinical experiences with IFN protein therapy for many other solid cancers have generally not been encouraging. In the conventional regimen of IFN clinical trials, the recombinant IFN-α protein is systemically administered through subcutaneous or intramuscular routes. However, since the protein is rapidly degraded in the blood circulation and only 0.01% of subcutaneously injected IFN-α can reach the target organs, the delivery of the IFN-α protein might be insufficient and/or result in an unsustainable level in the tumor site, which may be the cause of the diminished antitumor effect in previous clinical trials based on the IFN-α protein. In contrast, since gene transfer allows an increased and sustained local concentration of IFN-α in the target sites with minimal leakage of the cytokine into the systemic blood circulation, the use of IFN-α is expected to improve the therapeutic effect and safety in the context of gene therapy.

In fact, we previously demonstrated that intratumoral injection of IFN-α expressing adenovirus vector induced the direct cytotoxicity in the pancreatic cancer (US 2005/0260167 A1). In addition, the gene transfer of IFN-α augmented antitumor immunity by a stimulation of natural killer (NK) cells and cytotoxic T lymphocytes and the maturation of antigen-presenting cells. Therefore, we expect that an IFN-A gene transfer could enhance the GVT effect by promoting recognition of TAAs by the donor immune system in alloHSCT recipients, and also that alloHSCT, on the other hand, could augment the therapeutic efficacy of an IFN-α gene transfer by providing a "fresh" immune system in which tolerance to tumor cells is not yet induced. In this study, using an MHC (H-$2^d$)-matched mouse alloHSCT model, we found that an intratumoral IFN-α gene transfer significantly enhanced the antitumor effects of alloHSCT against a murine colon and renal cancer. Importantly, GVHD was not exacerbated in any of the treated mice, suggesting the augmentation of tumor-specific immunity of donor T cells by the IFN-α gene transfer.

SUMMARY OF THE INVENTION

The present invention provides a method of treating a solid tumor comprising conducting allogeneic hematopoietic stem cell transplantation and conducting IFN-α gene therapy at a local site in or around the tumor (i.e., intratumorally or peritumorally), a therapeutic composition used for said method and the like.

According to the present invention, a synergistic and potent antitumor effect on an intractable solid tumor such as colon cancer or renal cancer can be accomplished by allogeneic hematopoietic stem cell transplantation and administration of an IFN-α gene. This antitumor effect is observed for a tumor at a distant site to which the gene has not been administered. Thus, the present invention is particularly effective in that it can induce a systemic antitumor immune reaction.

The present invention relates to the following.

[1] A method of treating a solid tumor in a mammal, comprising:
 subjecting the mammal to allogeneic hematopoietic stem cell transplantation; and
 administering a vector expressing interferon-alpha to the mammal.
[2] The method according to [1], wherein the growth of the solid tumor is suppressed.
[3] The method according to [1], wherein said vector is a virus vector.
[4] The method according to [3], wherein said virus vector is an adenovirus vector.
[5] The method according to [1], wherein said vector is locally injected into the solid tumor or a portion surrounding the solid tumor.
[6] The method according to [1], wherein said solid tumor is selected from the group consisting of colon cancer, renal cancer, pancreatic cancer, esophageal cancer bladder cancer, prostate cancer, head and neck cancer, gastric cancer, lung cancer, hepatocellular carcinoma and melanoma.
[7] The method according to [4], wherein said adenovirus vector is administered at a dose ranging from $5\times10^6$ to $2.5\times10^9$ pfu/g of tumor weight/day.

DETAILED DESCRIPTION OF THE INVENTION

Figure 1:
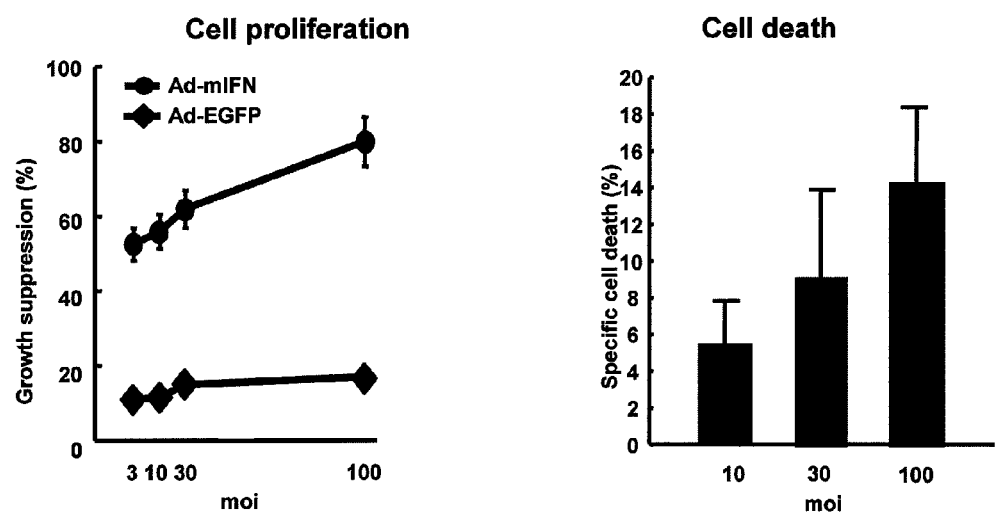
FIG. 1 shows growth inhibition and cell death in Renca cells induced by the infection of IFN-alpha adenovirus.

The present invention is described in detail below.

According to the present invention, allogeneic hematopoietic stem cell transplantation (alloHSCT) can be conducted in a mammal according to those conventionally conducted for treatments of hematopoietic malignancies such as leukemia. Any mammal such as human, monkey, cow, horse, sheep, rabbit, dog, cat, rat or mouse may be used according to the present invention. As used herein, the term "allogeneic" refers to individuals belonging to the same species but having genetic backgrounds different from each other. Hematopoietic stem cells used in allogeneic hematopoietic stem cell transplantation can be collected from bone marrow or peripheral blood of an allogeneic individual such as a human (donor) other than the patient (recipient). Preferably, hematopoietic stem cells are collected from a donor having major histocompatibility complex (MHC) that matches that of the recipient. Furthermore, umbilical cord blood can also be used according to the present invention. If hematopoietic stem cells are to be collected from peripheral blood, the collection may be carried out using a blood component collection apparatus or the like after recruiting hematopoietic stem cells in the peripheral blood using granulocyte colony-stimulating factor (G-CSF). A sufficient amount of hematopoietic stem cells are transplanted for allogeneic hematopoietic stem cell transplantation. Usually, an amount corresponding to $2 \times 10^8$ nucleated cells/kg is transplanted in case of bone marrow or umbilical cord blood. In case of peripheral blood, the amount corresponds to $2.5 \times 10^6$ or more, desirably 4 to $5 \times 10^6$ or more CD34-positive cells/kg of patient's body weight.

Prior to the transplantation, treatment called pretransplanting treatment with a combination of an anticancer agent, an immunosuppressive agent, total body irradiation (TBI) and the like is conducted from 7 to 4 days before the transplantation, aiming at complete elimination of tumor cells. Various method are carried out for the pretreatment, for example, cyclophosphamide and TBI; busulfan and cyclophosphamide; fludarabine and TBI; fludarabine and melphalan; and fludarabine, busulfan and antithymocyte globulin.

According to the present invention, administration of a gene encoding interferon-alpha (IFN-α) is carried out in addition to allogeneic hematopoietic stem cell transplantation. IFN-α is not limited to a single subtype among the known 13 subtypes (α1, 2, 4, 5, 6, etc.) which are classified on the basis of the specificities. Genes encoding such IFN-α are known and may be prepared according to a conventional method.

Any vector that is suitable for high expression of an IFN-α gene at a local site may be used as the vector used for administering the IFN-α gene. Either a non-virus vector or a virus vector may be used. Examples of the non-virus vectors include plasmid vectors encapsulated in liposomes or the like. There is no specific limitation concerning the virus vector. A known vector generally used for gene transfer can be used. Examples thereof include adenovirus vectors, retrovirus vectors, lentivirus vectors, adeno-associated virus vectors and Sendai virus vectors. The virus vector is preferably replication-defective. A method in which an adenovirus vector or a Sendai virus vector, which results in superior gene transfer efficiency, is used exemplifies one preferred embodiment of the present invention. Several serotypes are known for adenovirus vectors. Although it is not intended to limit the present invention, one derived from type 2, type 5 or type 35 is preferable. As a nonproliferative adenovirus vector, one lacking the E1 region can be preferably used. SeV/dF which lacks the fusion gene (F) can be preferably used as a Sendai virus vector.

The IFN-α gene is incorporated into a vector under the control of an appropriate promoter so that IFN-α can be expressed in cells at the administration site. Such promoters include, but are not limited to, CAG promoter (Gene, Vol. 108, p. 193-199 (1991)), cytomegalovirus promoter, SV40 promoter and 3-phosphoglycerate kinase (PGK) promoter. Furthermore, a known regulatory element such as a terminator or an enhancer may be attached to the vector.

The present invention can be applied to a solid tumor for which the IFN-α gene can be administered into the tumor or a portion surrounding the tumor. Although it is not intended to limit the present invention, the present invention exhibits a growth suppression effect on and is effective, for example, for an intractable solid tumor such as colon cancer, renal cancer, pancreatic cancer, esophageal cancer, bladder cancer, prostate cancer, head and neck cancer, gastric cancer, lung cancer, hepatocellular carcinoma or melanoma.

The dose of the IFN-α gene to be administered in or around the tumor may be any one as long as the efficacy is exhibited and can be appropriately determined depending on the IFN-α gene-containing vector to be used. For example, an adenovirus vector containing an IFN-α gene (Ad-IFNα) is administered at a dose of $5 \times 10^6$ to $2.5 \times 10^9$, preferably $5 \times 10^7$ to $2.5 \times 10^8$ pfu/g of tumor weight/day.

There is no specific limitation concerning the route of administration of the IFN-α gene. For example, the IFN-α gene-containing vector is administered to a patient into the tumor or a portion surrounding the tumor by injection, and the formulation for administration is preferably formulated into an injectable preparation suitable for the IFN-α gene-containing vector to be used. For example, in case of a virus vector, such a formulation can be prepared as a solution formulation by mixing with a pharmaceutically acceptable carrier. A formulation in which a virus vector is suspended in injectable distilled water, physiological saline or phosphate buffered saline exemplifies one embodiment of the present invention. Furthermore, the formulation may contain a component for stabilizing the active ingredient (glycerol, sugar, etc.), a component for adjusting the osmotic pressure, an antimicrobial agent or the like.

According to the present invention, immune cells transfused at the allogeneic hematopoietic stem cell transplantation exert a graft-versus-tumor (GVT) effect to cause growth suppression and regression of the tumor. The tumor is killed by the action of IFN-α expressed from the IFN-α gene transferred into the tumor or a portion surrounding the tumor, resulting in exposure of the tumor antigen. Then, recognition of the tumor antigen by the transplanted lymphocytes is promoted, and an immune response to the tumor can be induced. Furthermore, the lymphocytes are activated and proliferated by the action of the expressed IFN-α itself. The present invention has a remarkable therapeutic effect of suppressing cancer (tumor) growth and promoting regression by synergistically exerting the GVT effect due to the allogeneic hematopoietic stem cell transplantation, and the antitumor effect and the tumor-specific immune reaction-inducing effect by IFN-α expressed from the administered IFN-α gene as described above.

The treatment method of the present invention is characterized in that IFN-α can exert the direct antitumor effect which induces prominent death of tumor cells as well as diverse antitumor modes including induction of systemic specific tumor immunity effects by activation of NK cells or cytotoxic T cells and activation/maturation promotion of antigen-presenting cells, and suppression of tumor angiogenesis. Thus, it is possible according to the method of the present invention to potently control a tumor at a local site and to deal with systemic metastasis. This is apparent from the fact that the method of the present invention exhibits the therapeutic effects also on other tumors to which the IFN-α gene has not been administered as described in Examples below. Furthermore, since most IFN-α expressed in the tumor is not leaked into blood, the present invention is highly safe. This is also one of advantages of the present invention.

Practically, solid tumors exhibit resistance to immunotherapies in many clinical cases. This is due to acquisition of immunosuppressive environment by the tumors as a result of induction of regulatory T cells or influence by cytokines. This problem associated with conventional immunotherapy is solved by the destruction of the immunosuppressive environment by pretransplanting treatment prior to allogeneic hematopoietic stem cell transplantation.

The present invention further provides a composition for treating a solid tumor composed of the IFN-α gene-containing vector formulation which is prepared for use in combination of allogeneic hematopoietic stem cell transplantation. The formulation can be converted into a kit for treating a solid tumor, for example, by combining it with an agent that is used for pretransplanting treatment.

EXAMPLES

The following Examples illustrate the present invention in more detail, but are not to be construed to limit the scope thereof.

Materials and Methods

Animals and Transplantation

Seven-to-nine-week-old female BALB/c ($H-2^d$, Ly-1.2) and DBA/2 ($H-2^d$ Ly-1.1) mice were purchased from Charles River Japan, Inc. (Kanagawa, Japan), and were housed under sterilized conditions. Nine-to-ten-week-old BALB/c mice received a lethal dose (9 Gy) of total body irradiation on the day of transplantation. The irradiated BALB/c mice were injected intravenously with $5 \times 10^6$ of T cell-depleted bone marrow (BM) cells and $2 \times 10^6$ splenic T cells from donor DBA/2 mice in a total volume of 0.2 ml Dulbecco's phosphate buffered saline solution (PBS). BM cells were isolated from donors by flushing each femur and tibia with RPMI-1640 medium (RPMI) supplemented with 5% heat-inactivated fetal bovine serum (FBS) (ICN Biomedicals, Inc., Irvine, Calif.), and splenic cells were prepared by macerating the spleens with a pair of tweezers. After lysis of the erythrocytes, the BM and splenic cells were incubated with anti-Thy-1.2 immunomagnetic beads (Miltenyi Biotec, Bergisch Gladbach, Germany) at 4° C. for 15 min, followed by depletion and selection of T cells by AutoMACS (Miltenyi Biotec), respectively. More than 90% of T cells were depleted from the BM cells.

Tumor Cell Lines and Recombinant Adenovirus Vectors

CT26 and Renca are weakly immunogenic BALB/c-derived colon and renal cancer cell lines, respectively, and were obtained from the American Type Culture Collection (ATCC, Rockville, Md.). Both cell lines were confirmed to express MHC class I molecules ($H-2K^d$ and $H-2D^d$) abundantly by flow cytometry (data not shown). Cells were maintained in RPMI containing 10% FBS, 2 mM L-glutamine, and 0.15% sodium bicarbonate (complete RPMI). The recombinant adenovirus vectors expressing mouse interferon-α (Ad-mIFN), enhanced green fluorescein protein (Ad-EGFP), alkaline phosphatase cDNA (Ad-AP) and no gene (Ad-ΔE1) were prepared. The recombinant adenoviruses are Ad5 defective with a deletion in E3 region, and have the CAG promoter, which is a hybrid of the cytomegalovirus immediate early enhancer sequence and the chicken β-actin/rabbit β-globin promoter. A cesium chloride-purified virus was desalted using a sterile Bio-Gel P-6 DG chromatography column (Econopac DG 10, BioRad, Hercules, Calif.) and diluted for storage in a 13% glycerol/PBS solution. All viral preparations were confirmed to be free of $E1^+$ adenovirus by PCR assay.

In Vitro Cell Proliferation Assay

Renca cells were seeded at $2 \times 10^3$ per well in 96-well plates and infected with Ad-mIFN or Ad-EGFP at moi of 3, 10, 30 and 100. The cell numbers were assessed by a calorimetric cell viability assay using a water-soluble tetrazolium salt (Tetracolor One; Seikagaku Corp., Tokyo, Japan) 5 days after the infection. The absorbance was determined by spectrophotometry using a wavelength of 450 nm with 595 nm as a reference. The assays (carried out in 8 wells) were repeated a minimum of two times and the mean±standard deviation was plotted. The data were expressed as the percent growth suppression, which was determined by the formula:

$$\{1-(\text{OD450 of Ad-mIFN-infected cells/OD450 of Ad-EGFP-infected cells})\} \times 100.$$

Annexin V Assay

Cultured cells were infected with Ad-mIFN or Ad-Δ1 in a 6-cm dish, and 3 days later prepared by the treatment of 2 mM EDTA and then stained with annexin-V-FITC (Medical & Biological Laboratories Co. LTD., Nagoya, Japan), which detects phosphatidylserine of inverted plasma membranes, and then were examined by FACS analysis. The assays were carried out in triplicate, and the mean±standard deviation was plotted. The data were expressed as the specific cell death (%) (cell death fraction induced by virus infection (%)—that by mock infection (%)).

In Vivo Tumor Inoculation and IFN-α Gene Transfer

Tumor cells were prepared in a total volume of 50 μL PBS ($5 \times 10^6$ of Renca and $1 \times 10^6$ of CT26 cells) and injected subcutaneously on the leg. When the subcutaneous tumor was established (~0.6 cm in diameter), 50 μl of Ad-mIFN or control vector was once injected into the tumors. The shortest (r) and longest (l) tumor diameters were measured at indicated days and the tumor volume was determined as $r^2 l/2$.

ELISpot Assays

IFN-γ ELISpot kits (BD Bioscience) were used according to the manufacturer's instructions. Briefly, splenocytes ($1 \times 10^5$) and 30 Gy-irradiated Renca ($5 \times 10^4$) cells were co-cultured in 96-well plates pre-coated with mouse IFN-γ (BD Bioscience) for 20 hours at 37° C. in complete RPMI medium in triplicate. After aspirating the cell suspension and washing wells with deionized water, biotinylated anti-mouse IFN-γ antibody (2 μg/mL) was added and incubated for 2 hours at room temperature. After extensive washing, a streptavidin-horseradish peroxidase solution was added and incubated for 1 hour at room temperature. After washing, an aminoethyl carbozole substrate solution was added, and the plate was incubated for 15 minutes. Spots were counted under a stereomicroscope after washing the plate.

Immunohistochemistry

Immunostaining was performed using the streptavidin-biotin-peroxidase complex techniques (Nichirei, Tokyo, Japan). Consecutive cryostat tissue sections (5 μm) were mounted on glass slides and fixed in cold acetone (−20° C.) for 5 minutes. After blocking with normal rat serum, the sections were stained with rat anti-mouse CD4 and CD8 antibodies (BD PharMingen). Parallel negative controls without primary antibodies were examined in all cases. The sections were counter-stained with hematoxylin.

Evaluation of GVHD

The degree of clinical GVHD in transplant recipients was assessed weekly by a scoring system that sums changes in five parameters: weight loss, posture, activity, fur texture, and skin integrity (each parameter was scored from 0 to 2 and the maximum index was 10). In some recipients, selected serum chemistry was also examined for evaluation of GVHD.

Statistical Analysis

Comparative analyses of the data were performed by the Student t-test, using SPSS statistical software (SPSS Japan Inc., Tokyo, Japan). $P<0.05$ was considered as a significant difference.

Example 1

Cytotoxic Effect of Interferon-α Gene Transduction into Renal Cancer Cells

To study whether the expression of the IFN-α gene effectively inhibits cell-growth, Renca cells were infected with the Ad-mIFN adenovirus vector. The infection with Ad-mIFN inhibited cell growth (FIG. 1 left panel) and induced cell death in the Renca cells (FIG. 1 right panel). The TUNEL staining confirmed the IFN-α-induced apoptosis in the cells.

Example 2

Antitumor Effect of Human IFN-α Gene Transduction into Subcutaneous Tumors

Figure 2:
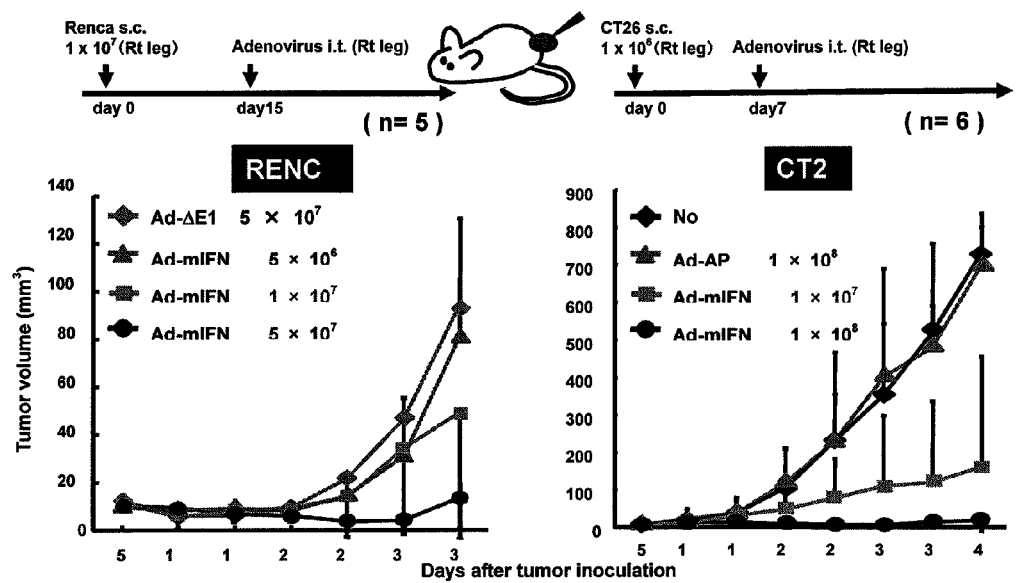
FIG. 2 shows antitumor effect shown by the intratumoral injection of IFN-alpha adenovirus against Renca and CT26 cells.

To examine the in vivo antitumor effect of the IFN-α gene therapy, various amounts of Ad-mIFN were injected into Renca and CT26 subcutaneous tumors. The single injection of Ad-mIFN showed remarkable tumor suppressive effects in both tumors in a dose-dependent manner (FIG. 2).

Example 3

AlloHSCT Causes GVHD and GVT Effects

We first assessed the post-transplant immune reconstitution of T cells and donor chimerism of splenic $CD3^+$ T cells in alloHSCT recipients (DBA/2→BALB/c). The reconstitution of both $CD4^+$ and $CD8^+$ T cells was delayed in alloHST recipients compared with that in syngeneic HSCT recipients at 8 weeks post transplantation, which was consistent with other reports. The early ($\leq 2$ w) post-transplant mortality, most likely due to acute GVHD or graft failure, was usually less than 15% in transplant recipients. Analysis of donor engraftment showed 95.7±1.5% donor type in alloHSCT recipients (n=3) at 8 weeks post transplantation.

Figure 3:
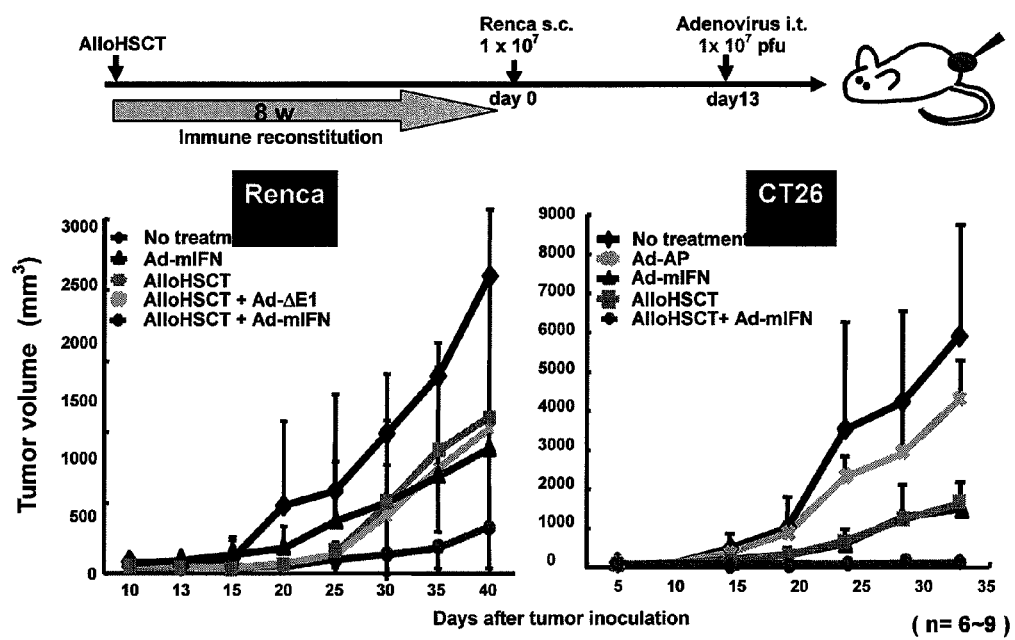
FIG. 3 shows enhancement of antitumor effect in alloHSCT mice by IFN-alpha gene transfer.

We then examined whether our alloHSCT models generate any GVHD and GVT effects. The clinical score of GVHD severity at 8 weeks was approximately 4 in alloHSCT recipients, whereas it was less than 1 in synHSCT recipients. Death from GVHD was rarely observed during the first 3 months after the transplantation. For evaluation of GVT effects, $1\times10^6$ CT26 or $5\times10^6$ Renca cells were subcutaneously inoculated into the mice 8 to 9 weeks post transplantation. The growth of the tumors was significantly suppressed in the alloHSCT recipients compared with that in the naïve mice (FIG. 3). Our alloHSCT model was shown to cause constantly GVHD and a limited but detectable level of the GVT effect, which is highly similar to a clinical setting after allogeneic HSCT.

Example 4

IFN-α Gene Transfer Induces Synergistic Antitumor Effect with alloHSCT

To examine whether IFN-α gene transfer could enhance the antitumor effects of alloHSCT, the mice were inoculated subcutaneously with CT26 or Renca cells at 8 weeks post transplantation, and $1\times10^7$ PFU of Ad-mIFN was once injected into the tumor 13 days after the inoculation. The tumor volumes at the injection were approximately 60-100 $mm^3$. In this experiment, since the strong antitumor effect of high dose ($5$-$10\times10^7$ PFU) of Ad-mIFN would make the synergistic effect of IFN-α gene transfer in the transplanted mice unclear, $1\times10^7$ PFU of Ad-mIFN was employed. The Ad-mIFN injection showed some suppressive effect in naive mice, whereas significant suppression of tumor growths was recognized in alloHSCT recipients (FIG. 3). The results demonstrated that IFN-α gene transfer can augment the antitumor effects of donor immune cells in the context of alloHSCT.

Example 5

Figure 4:
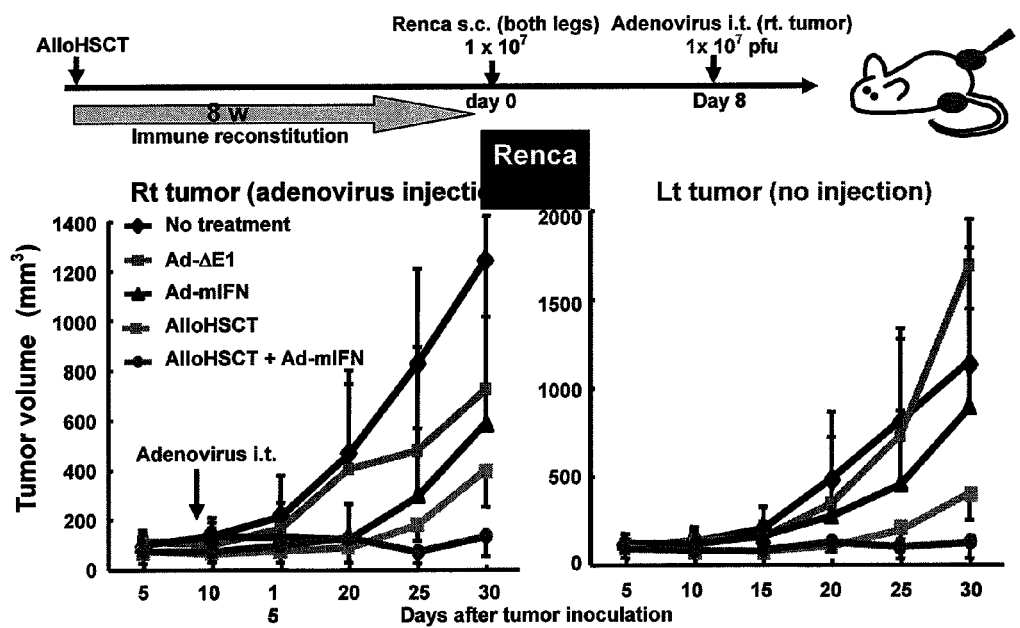
FIG. 4 shows IFN-alpha gene delivery into tumors on one leg of the mice having tumors on both legs.

IFN-α Gene Transfer Causes Growth Suppression of Both Local and Distant Tumors in alloHSCT Recipients Next, to evaluate the therapeutic efficacy of IFN-α gene transfer for tumors at distant sites, transplant recipients were subcutaneously inoculated with $5\times10^6$ Renca cells on both legs and, 8 days later only the right leg tumor was then injected with $1\times10^7$ PFU of Ad-mIFN. In alloHSCT recipients, significant tumor suppression of the treated tumor on the right leg and the untreated tumor on the opposite leg was observed (FIG. 4), which demonstrated that IFN-α gene transfer causes a systemic antitumor immunity in alloHSCT recipients.

Example 6

$CD4^+$ and $CD8^+$ T Cells Contribute to Antitumor Immunity

Figure 5:
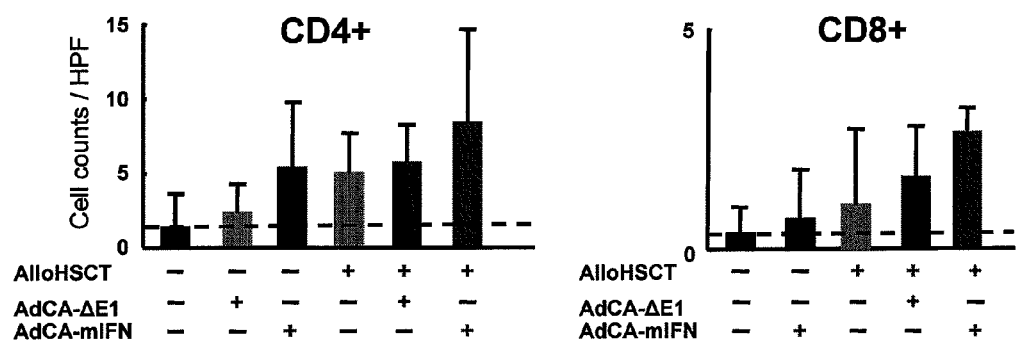
FIG. 5 shows infiltration of CD4+ and CD8+ T cells into S.C. tumors.
Figure 6:
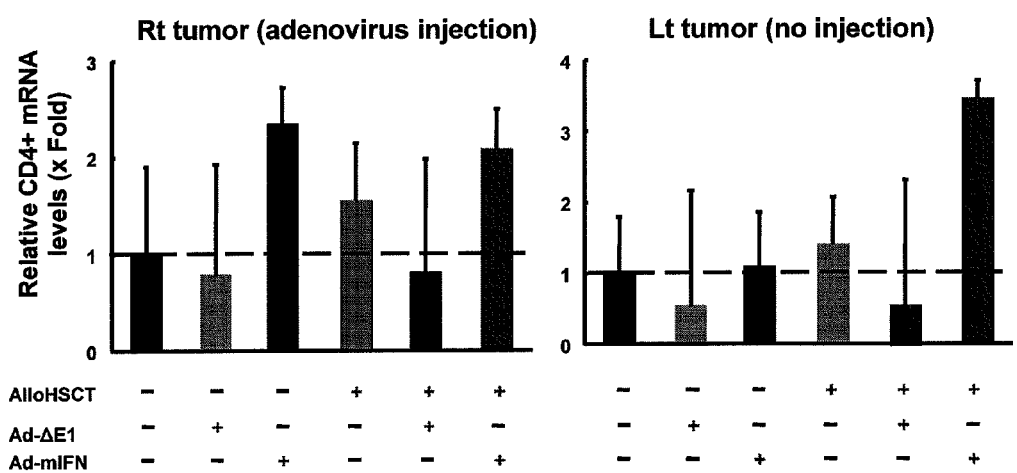
FIG. 6 shows infiltration of CD4+ T cells into S.C. tumors infected with IFN-alpha adenovirus.

To explore the role of immune cells in antitumor immunity in vivo, the $CD4^+$ and $CD8^+$ T cells were examined by the immunohistochemical staining. The staining showed that $CD4^+$ and $CD8^+$ T cells infiltrated into the Renca subcutaneous tumors in alloHSCT recipients, and that the IFN-α gene transfer increased the number of these cells within the tumor (FIG. 5). Real time RT-PCR analysis showed that the CD4 expression was elevated in non-treated tumors at the opposite site after the injection of Ad-mIFN in alloHSCT recipients (FIG. 6).

Example 7

Figure 7:
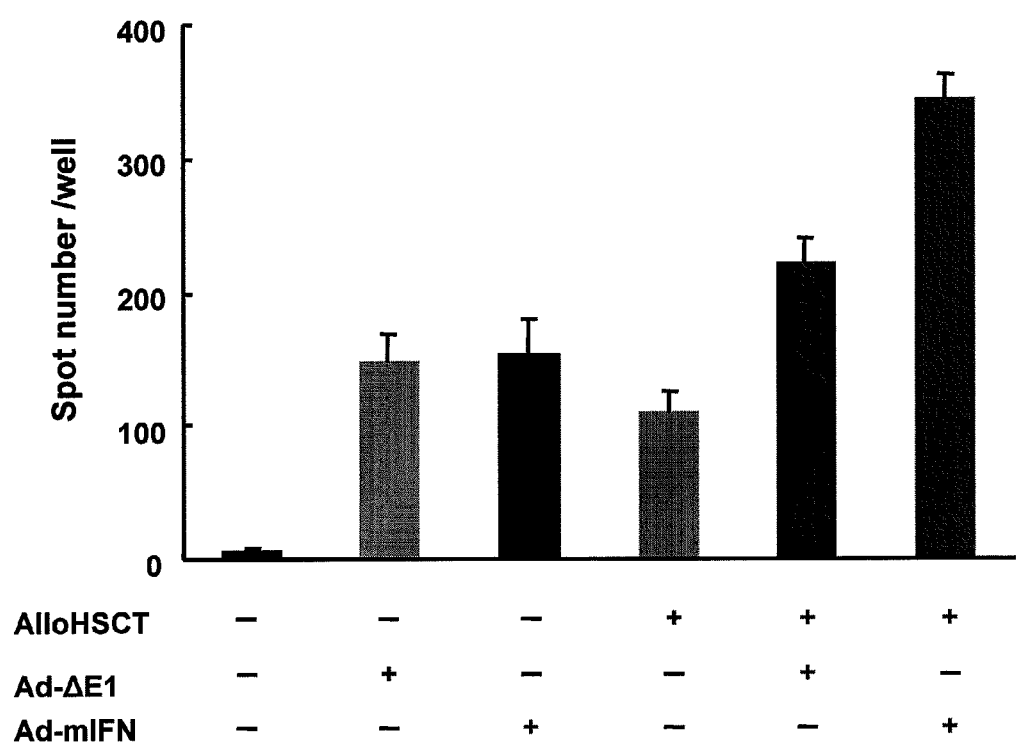
FIG. 7 shows increase of tumor-reactive cells by intratumoral IFN-alpha adenovirus injection in alloHSCT recipients.

Expansion of Tumor-Specific T Cells After Intratumoral IFN-α Gene Transfer in alloHSCT Recipients To examine the immune reaction to the IFN-α gene transfer in alloHSCT recipients, the frequency of tumor-reactive T cells was determined by ELISpot assay. The average numbers of IFN-γ secreting spots in response to Renca stimulation were clearly increased in alloHSCT recipients, and IFN-α gene transfer further increased the spot numbers for Renca cells (FIG. 7).

Example 8

IFN-α Gene Transfer does not Exacerbate GVHD

Figure 8:
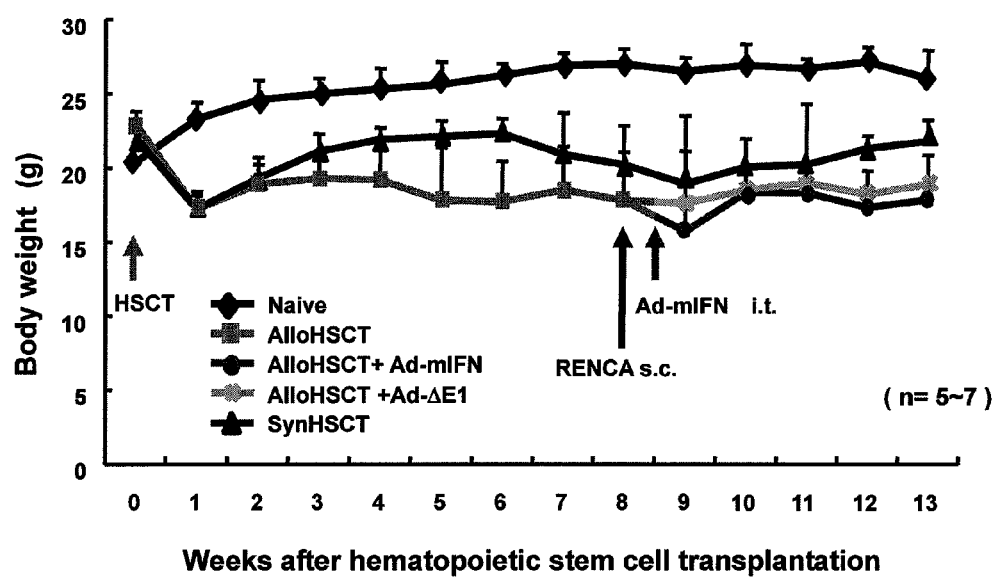
FIG. 8 shows body weights of alloHSCT recipients mice after IFN-alpha gene transfer.

IFN-α expression in tumor cells could theoretically promote a donor T cell response not only against TAAs but also against mHAs shared by tumor and normal cells, which might result in GVHD exacerbation. We thus examined serum chemistry and the body weight in the transplanted mice with the IFN-α gene transfer. Albumin, total bilirubin, aspartate aminotransferase (AST), alanine aminotransferase (ALT), and creatinine (Cre) are the potential indicators of GVHD-related injury of the hepatobiliary system and so no. The body weight is an indicator of total clinical GVHD. GVHD was not serologically nor clinically exacerbated in the IFN-α gene-transduced mice compared with the control vector-injected mice (FIG. 8 and Table 1).

TABLE 1

|  | ALB (g/dl) | T-bil (g/dl) | AST (IU/L) | ALT (IU/L) | Cr (mg/dl) |
|---|---|---|---|---|---|
| No treatment | 3.3 ± 0.2 | 0.09 ± 0.01 | 220 ± 238 | 80 ± 81* | 0.12 ± 0.02 |
| Ad-mIFN | 3.2 ± 0.2 | 0.06 ± 0.02 | 227 ± 116 | 152 ± 97 | 0.10 ± 0.01 |
| Ad-ΔE1 | 3.2 ± 0.2 | 0.06 ± 0.02 | 208 ± 68 | 111 ± 58 | 0.11 ± 0.04 |
| AlloHSCT + Ad-mIFN | 2.9 ± 0.1 | 0.07 ± 0.01 | 349 ± 110 | 107 ± 83 | 0.08 ± 0.02 |
| AlloHSCT + Ad-ΔE1 | 2.7 ± 0.1 | 0.05 ± 0.01 | 306 ± 58 | 286 ± 149* | 0.09 ± 0.01 |

*$P < 0.05$

All publications and patent documents cited herein are hereby incorporated by reference in their entity for all purposes to the same extent as if each were so individually denoted.

What is claimed is:

1. A method of treating a solid tumor in a mammal, comprising:
    subjecting the mammal to allogeneic hematopoietic stem cell transplantation; and
    injecting a vector expressing interferon-alpha into the solid tumor of the mammal.

2. The method according to claim 1, wherein the growth of the solid tumor is suppressed.

3. The method according to claim 1, wherein said vector is a virus vector.

4. The method according to claim 3, wherein said virus vector is an adenovirus vector.

5. The method according to claim 1, wherein said solid tumor is selected from the group consisting of colon cancer, renal cancer, pancreatic cancer, esophageal cancer bladder cancer, prostate cancer, head and neck cancer, gastric cancer, lung cancer, hepatocellular carcinoma and melanoma.

6. The method according to claim 4, wherein said adenovirus vector is administered at a dose ranging from $5 \times 10^6$ to $2.5 \times 10^9$ pfu/g of tumor weight/day.

* * * * *